US008123710B2

(12) United States Patent
Chan

(10) Patent No.: US 8,123,710 B2

(45) Date of Patent: Feb. 28, 2012

(54) LIMITING CONNECTOR FOR KNEE BRACE

(76) Inventor: Shu-Chen Chan, Fengyuan (TW)

( * ) Notice: Subject to any disclaimer, the term of this patent is extended or adjusted under 35 U.S.C. 154(b) by 395 days.

(21) Appl. No.: 12/502,032

(22) Filed: Jul. 13, 2009

(65) Prior Publication Data

US 2011/0009786 A1 Jan. 13, 2011

(51) Int. Cl.
*A61F 5/00* (2006.01)
*A61F 5/37* (2006.01)
*E05D 11/10* (2006.01)

(52) U.S. Cl. .............. 602/16; 602/23; 602/26; 128/882; 16/324; 16/326

(58) Field of Classification Search ................ 602/5, 12, 602/16, 20–22, 23–27; 128/878, 881–882; 16/354, 371, 374–377, 321, 324–326, 332, 16/334, 348–349, 352; 403/93, 96–97, 101; 74/575–578, 551.3–551.7, 526–530
See application file for complete search history.

(56) References Cited

U.S. PATENT DOCUMENTS 4,817,588 A * 4/1989 Bledsoe .......................... 602/16
5,997,493 A * 12/1999 Young .............................. 602/16
7,024,727 B1 * 4/2006 Huang et al. .................... 16/354
7,833,181 B2 * 11/2010 Cormier et al. ................. 602/16
7,988,652 B2 * 8/2011 Chao .............................. 602/19
2006/0247565 A1 * 11/2006 Cormier et al. ................. 602/16

* cited by examiner

*Primary Examiner* — Patricia Bianco
*Assistant Examiner* — George N Phillips
(74) *Attorney, Agent, or Firm* — patenttm.us

(57) ABSTRACT

A limiting connector for a knee brace has a first arm, a second arm and an angle adjusting assembly. The second arm is connected pivotally to the first arm. The angle adjusting assembly is mounted between the first arm and the second arm, and has a positioning gear, a gear cap, two buttons and a rotating cap. The gear cap is mounted through the positioning gear and the second arm, and is mounted on the first arm to hold the positioning gear between the second arm and the gear cap. The buttons are selectively slid to engage the positioning gear and define a range of rotation between the first and second arms. The rotating cap is rotatably mounted through the gear cap, and pushes the positioning gear toward the first arm to disengage the positioning gear from the buttons for adjusting the range of rotation.

10 Claims, 8 Drawing Sheets

LIMITING CONNECTOR FOR KNEE BRACE

BACKGROUND OF THE INVENTION

1. Field of the Invention

The present invention relates to a brace, and more particularly to a limiting connector for a knee brace with a limiting dial to provide a fixed angle or an adjustable angle effect to support or train an injured knee joint.

2. Description of Related Art

With reference to FIG. 10, a conventional limiting connector for a knee brace comprises a first arm (71), a second arm (72) and a limiting dial (73).

The first arm (71) is connected to the second arm (72) at a pivot point. The limiting dial (73) is mounted at the pivot point between the arms (71,72) to limit movement angles between the arms (71,72), and has a lock (720), an adjusting plate (721) and multiple resilient stops (722). The lock (720) is connected to the first arm (71) and the second arm (72), and alternatively controls the arms (71,72) to a fixed angle condition or a pivoting condition.

The adjusting plate (721) is mounted on the first arm (71), and has multiple index slots (7210) formed radially in the adjusting plate (721) to define an angle index. The resilient stops (722) are connected pivotally to the first arm (71), extend out the adjusting plate (721) and engage the index slots (7210) in the adjusting plate (721).

Each resilient stop (722) has a mounting protrusion protruding toward the adjusting plate (721) and engaging one of the index slots (7210), and may be elastically pressed down and pivoted to mounted in one of the other index slots (7210) to define movement angles between the arms (71,72) range. However, the resilient stops (722) of the conventional limiting connector for knee brace easily disengage from the index slots (7210) by unintentionally shock allowing free movement of the arms (71,72) and maybe causing injury to a user.

To overcome the shortcomings, the present invention tends to provide a limiting connector for knee brace to mitigate or obviate the aforementioned problems.

SUMMARY OF THE INVENTION

The main objective of the invention is to provide a limiting connector for knee brace with a limiting dial and a knee brace comprising the same to provide a fixed angle or an adjustable angle effect and a supporting effect during rehabilitation.

A limiting connector for knee brace has a first arm, a second arm and an angle adjusting assembly. The second arm is connected pivotally to the first arm. The angle adjusting assembly is mounted between the first arm and the second arm, and has a positioning gear, a gear cap, two buttons and a rotating cap. The gear cap is mounted through the positioning gear and the second arm, and is mounted on the first arm to hold the positioning gear between the second arm and the gear cap. The buttons are slid to engage the positioning gear and define a range of rotation between the first and second arms. The rotating cap is rotatably mounted through the gear cap, and pushes the positioning gear toward the first arm to disengage the positioning gear from the buttons for adjusting the range of rotation.

Other objects, advantages and novel features of the invention will become more apparent from the following detailed description when taken in conjunction with the accompanying drawings.

DETAILED DESCRIPTION OF PREFERRED EMBODIMENT

Figure 1:
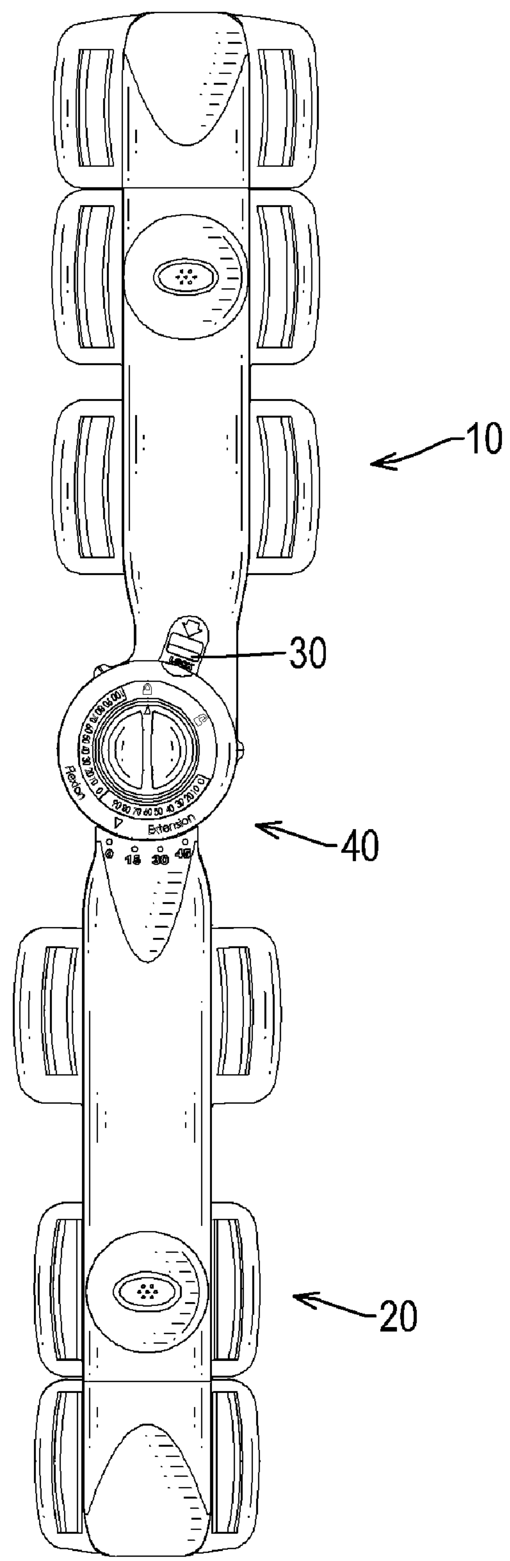
FIG. 1 is a side view of a limiting connector for a knee brace in accordance with the present invention.
Figure 2:
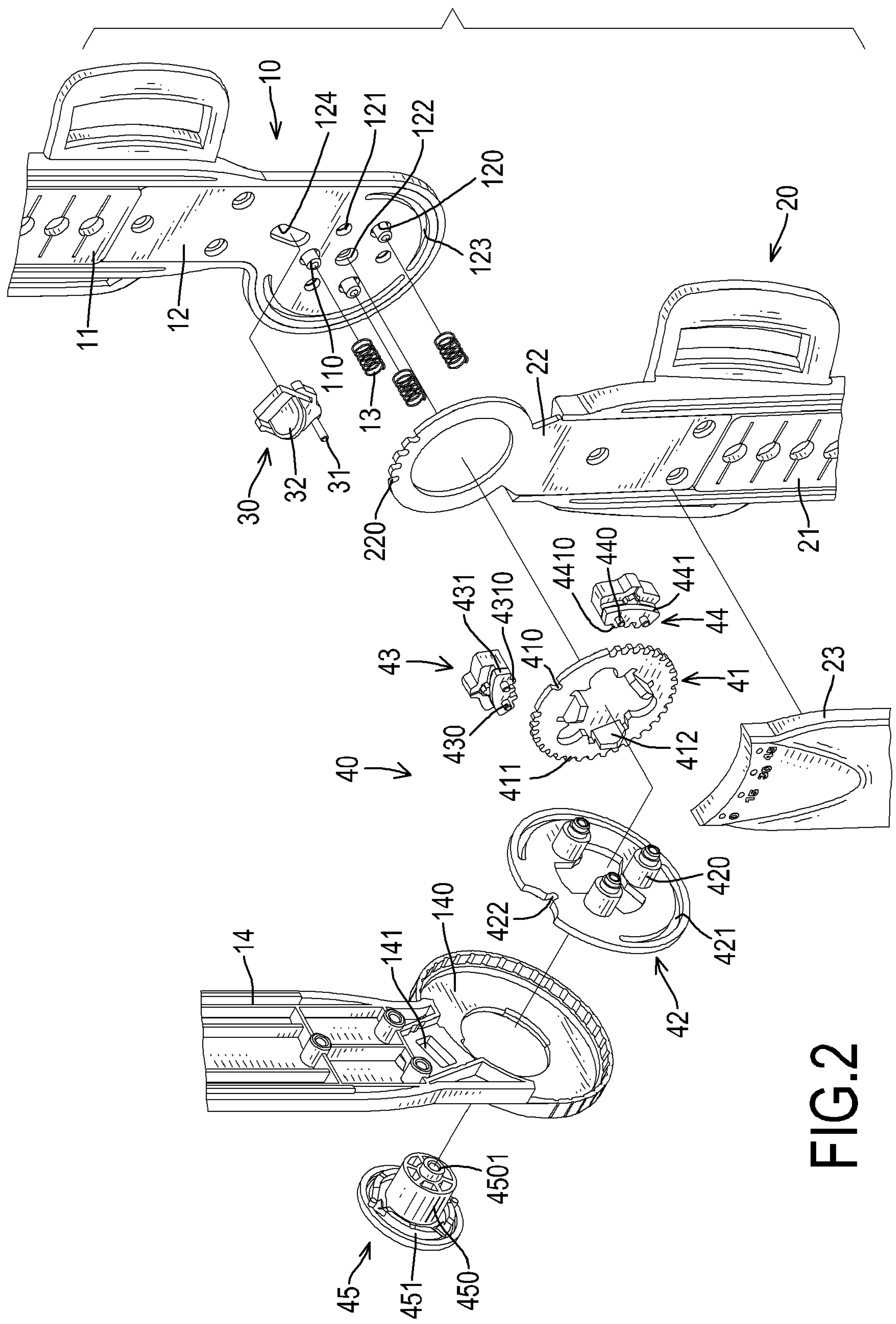
FIG. 2 is a partially exploded perspective view of the limiting connector for a knee brace in FIG. 1.

With reference to FIGS. 1 and 2, a limiting connector for a knee brace in accordance with the present invention has a first arm (10), a second arm (20), a lock (30) and an angle adjusting assembly (40).

The first arm (10) has a first board (11), a first pivoting element (12), three springs (13) and a first cover (14). The first board (11) is elongated and has a circular mounting end and three bars (110). The three bars (110) respectively protrude from the mounting end of the first board (11).

The first pivoting element (12) is mounted on the mounting end of the first board (11), and has three mounting holes (120), three fixing holes (121), an inserting hole (122), a first sliding groove (123) and a lock hole (124). The mounting holes (120) are formed through the first pivoting element (12) in a mounting circle and mounted respectively around the bars (110).

The fixing holes (121) are formed through the first pivoting element (12) in a fixing circle, and may have a center defined at the center of the mounting circle. The inserting hole (122) is formed through the first pivoting element (12) and may be defined at the center of the mounting circle or the fixing circle. The first sliding groove (123) is shaped in an arc and formed through the pivoting element (12) along a sliding circle having a sliding center, and may have two sliding rails respectively formed through the pivoting element (12). The lock hole (124) is elongated and formed through the pivoting element (12).

The springs (13) are mounted around the bars (110) and abut the first board (11). The first cover (14) is elongated and mounted on the first board (11), and has a cap (140) and an operating hole (141). The cap (140) is annular and mounted on the mounting end of the first board (11) and is marked as a graduated circle. The operating hole (141) is elongated and formed through the first cover (14) and is aligned with the lock hole (124).

The second arm (20) is connected pivotally to the first arm (10) and has a second board (21), a second pivoting element (22) and a second cover (23). The second board (21) is elongated. The second pivoting element (22) is mounted on the second board (21), and has an annular connecting end extending out the second board (21), mounted around the bars (110), mounted parallelly to the first pivoting element (12) and having an outer edge and multiple locking teeth (220). The multiple locking teeth (220) are formed in the outer edge of the second pivoting element (22) and are adjacent to the locking hole (124). The second cover (23) is elongated and mounted on the second board (21).

The lock (30) is moveably mounted in the lock hole (124) and extends out of the operating hole (141) and has a locking shaft (31) and a turning tab (32). The locking shaft (31) selectively engages one of the locking teeth (220) of the second pivoting element (22). The turning tab (32) protrudes from the lock (30) and extends out of the operating hole (141).

The angle adjusting assembly (40) is mounted between the first arm (10) and the second arm (20), and has a positioning gear (41), a gear cap (42), a first button (43), a second button (44) and a rotating cap (45).

Figure 3:
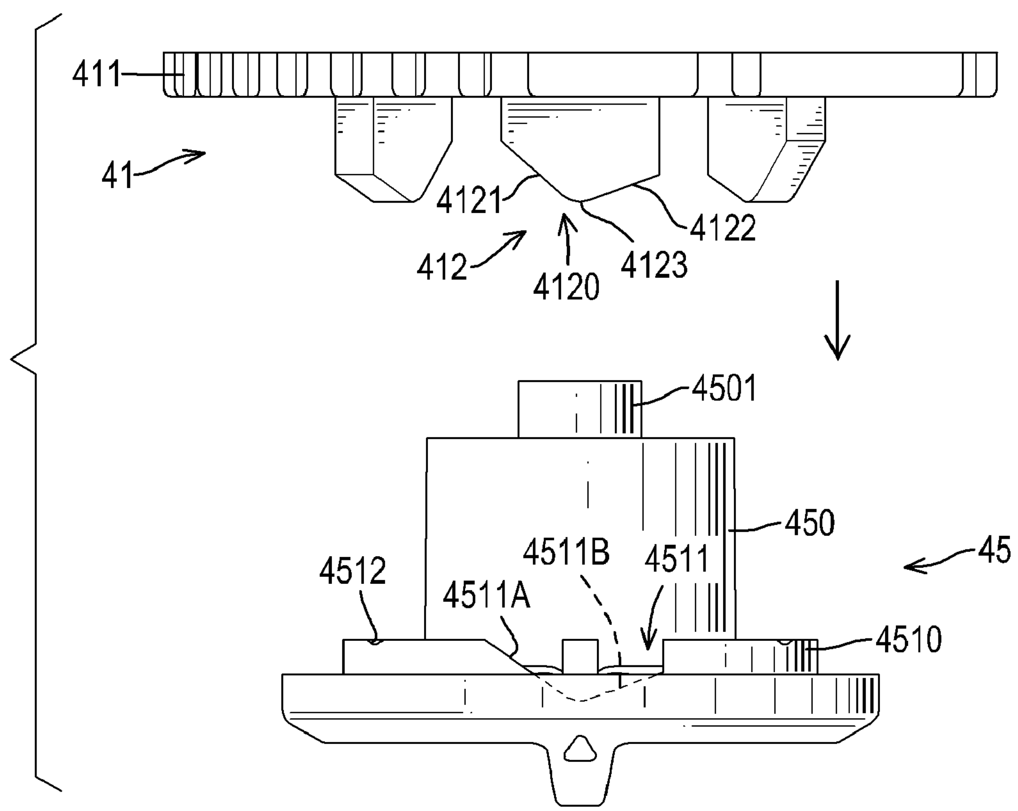
FIG. 3 is an exploded top view of a positioning gear and a rotating cap of the limiting connector for a knee brace in FIG. 2.

With further reference to FIG. 3, the positioning gear (41) is annular and mounted between the second pivoting element (22) and the cap (140) and abuts the springs (13) and has a pressing surface, an outer edge, an inner edge, a locking recess (410), multiple positioning teeth (411) and a pressing element (412). The pressing surface is defined opposite to the springs (13). The locking recess (410) is formed in the outer edge of the positioning gear (41) and aligns with one of the locking teeth (220) of the second pivoting element (22) and the locking shaft (31) of the lock (30). The positioning teeth (411) are formed in the outer edge of the positioning gear (41) and adjacent to the sliding groove (123).

The pressing element (412) is formed on the inner edge of the positioning gear (41) and has three pressing protrusions (4120). The pressing protrusions (4120) respectively protrude perpendicularly from the inner edge of the positioning gear (41) toward the first cover (14) and each pressing protrusion (4120) has a top, a first sliding surface (4121), a first guiding surface (4122), a positioning surface (4123) and a first stopping surface. The first sliding surface (4121) is formed slantwise on the top of the pressing protrusion (4120).

The first guiding surface (4122) is formed slantwise on the top of the pressing protrusion (4120), and has a length shorter than that of the first sliding surface (4121). The positioning surface (4123) is formed between the first sliding surface (4121) and the first guiding surface (4122). The first stopping surface perpendicularly extends from the inner edge and connects to the first guiding surface (4122) of the positioning gear (41).

The gear cap (42) is annular and mounted between the positioning gear (41) and the first cover (14), and is mounted around the pressing protrusions (4120), and has an inner edge, three fixing shafts (420), a sliding recess (421), an outer edge and a locking mount (422). The fixing shafts (420) protrude perpendicularly from the inner edge of the gear cap (42) toward the first pivoting element (12), and extend through the positioning gear (41) and the second pivoting element (22), and are mounted respectively in the fixing holes (121) of the first pivoting element (12).

The sliding recesses (421) are shaped as arcs and formed through the gear cap (42) along a cap circle, wherein the cap circle has a cap center aligning with the center of the sliding circle, and may have two sliding channels corresponding to the sliding rails of the sliding groove (123). The locking mount (422) is formed in the outer edge of the gear cap (42), and is aligned with the locking recess (410).

The first button (43) is mounted between the first pivoting element (12) and the gear cap (42), and has two first pins (430) and a first engaging slice (431). Each first pin (430) is mounted through the first button (43) and has two ends respectively and slidably extending into one of the sliding rails of the sliding groove (123) and a corresponding one of the sliding channels of the sliding recess (412). The first engaging slice (431) is mounted on the first button (43), and has two first engaging teeth (4310) protruding from the first engaging slice (431) and engaging the positioning teeth (411) of the positioning gear (41).

The second button (44) is mounted between the first pivoting element (12) and the gear cap (42), and has two second pins (440) and a second engaging slice (441). Each second pin (440) is mounted through the second button (44) and has two ends respectively and slidably extending into the other sliding rail of the sliding groove (123) and the other sliding channel of the sliding recess (412). The second engaging slice (441) is mounted on the second button (44), and has two second engaging teeth (4410) engaging with the positioning teeth (411) of the positioning gear (41).

The rotating cap (45) is mounted on the cap (140) of the first cover (14) and has an inner surface, a rotating shaft (450) and a pushing element (451). The rotating shaft (450) protrudes from the inner surface of the rotating cap (45), and is mounted through the cap (140) of the first cover (41), the gear cap (42), the positioning gear (41) and the second pivoting element (22), and has a protruding rod (4501). The protruding rod (4501) protrudes from the rotating shaft (450) toward the first pivoting element (12) and is mounted in the inserting hole (122) of the first pivoting element (12).

Figure 4:
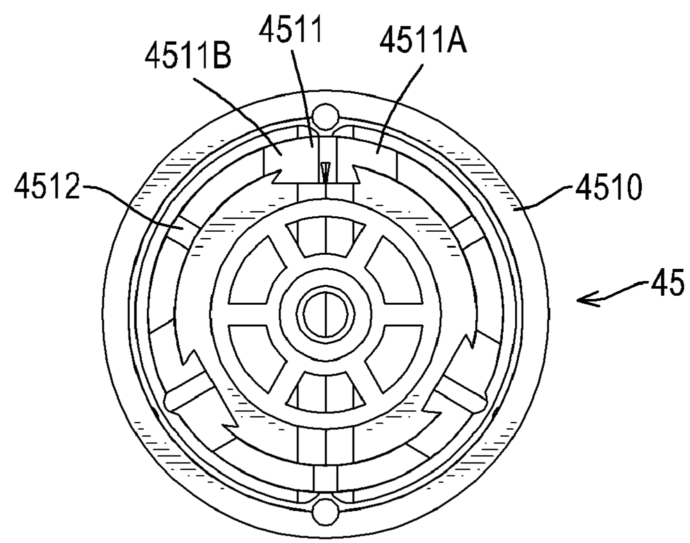
FIG. 4 is a side view of the rotating cap of the limiting connector for knee brace in FIG. 3.

With further reference to FIG. 4, the pushing element (451) has an annular wall (4510), three containing recesses (4511) and three fixing recesses (4512). The annular wall (4510) protrudes from the inner surface of the rotating cap (45) around the rotating shaft (450). The containing recesses (4511) are respectively formed in the annular wall (4510) and correspond respectively to the pressing protrusions (4120) of the positioning gear (41), and each containing recess (4511) has a second sliding surface (4511A), a second guiding surface (4511B) and a second stopping surface.

The second sliding surface (4511A) is formed slantwise in the containing recess (4511) and corresponds to the first sliding surface (4121) of the positioning gear (41). The second guiding surface (4511B) is formed slantwise in the containing recess (4511), and has a length shorter than that of the second sliding surface (4121), and corresponds to the first guiding surface (4122) of the positioning gear (41).

The second stopping surface is formed perpendicularly to the annular wall (4510), connected to the second guiding surface (4511B) and abuts the first stopping surface of the pressing protrusions (4120). The fixing recesses (4512) are formed in the annular wall (4510) respectively between each pair of adjacent containing recesses (4511), and may selectively engage respectively the positioning surfaces (4123) of the positioning gear (41).

The limiting connector for knee brace in accordance with the present invention provides two conditions in operation. The first condition is that the second arm (20) is adjusted to and kept at a fixed angle relative to the first arm (10). The second condition is that the second arm (20) is adjusted to be rotatable at a range of the swinging angle relative to the first arm (10).

Figure 5:
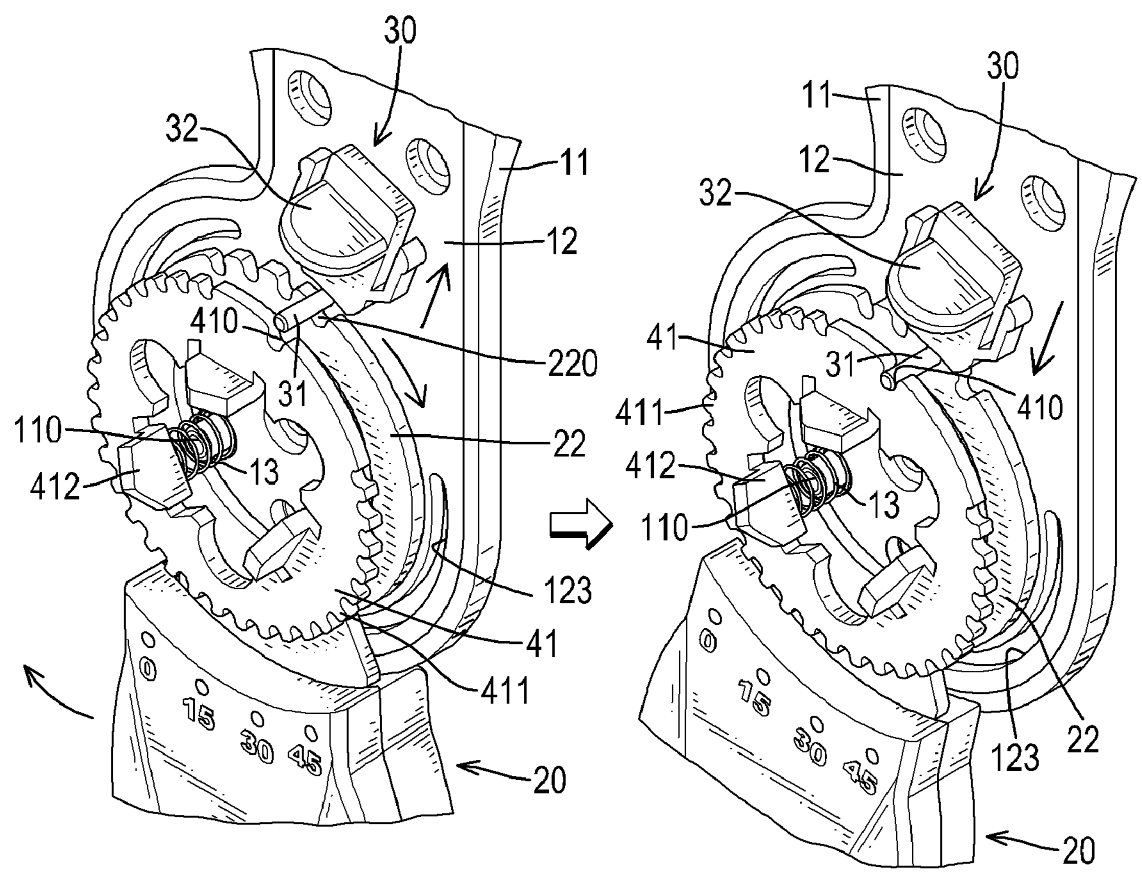
FIG. 5 is an enlarged operational perspective view showing the operation of a lock of the limiting connector for a knee brace in FIG. 2.
Figure 6:
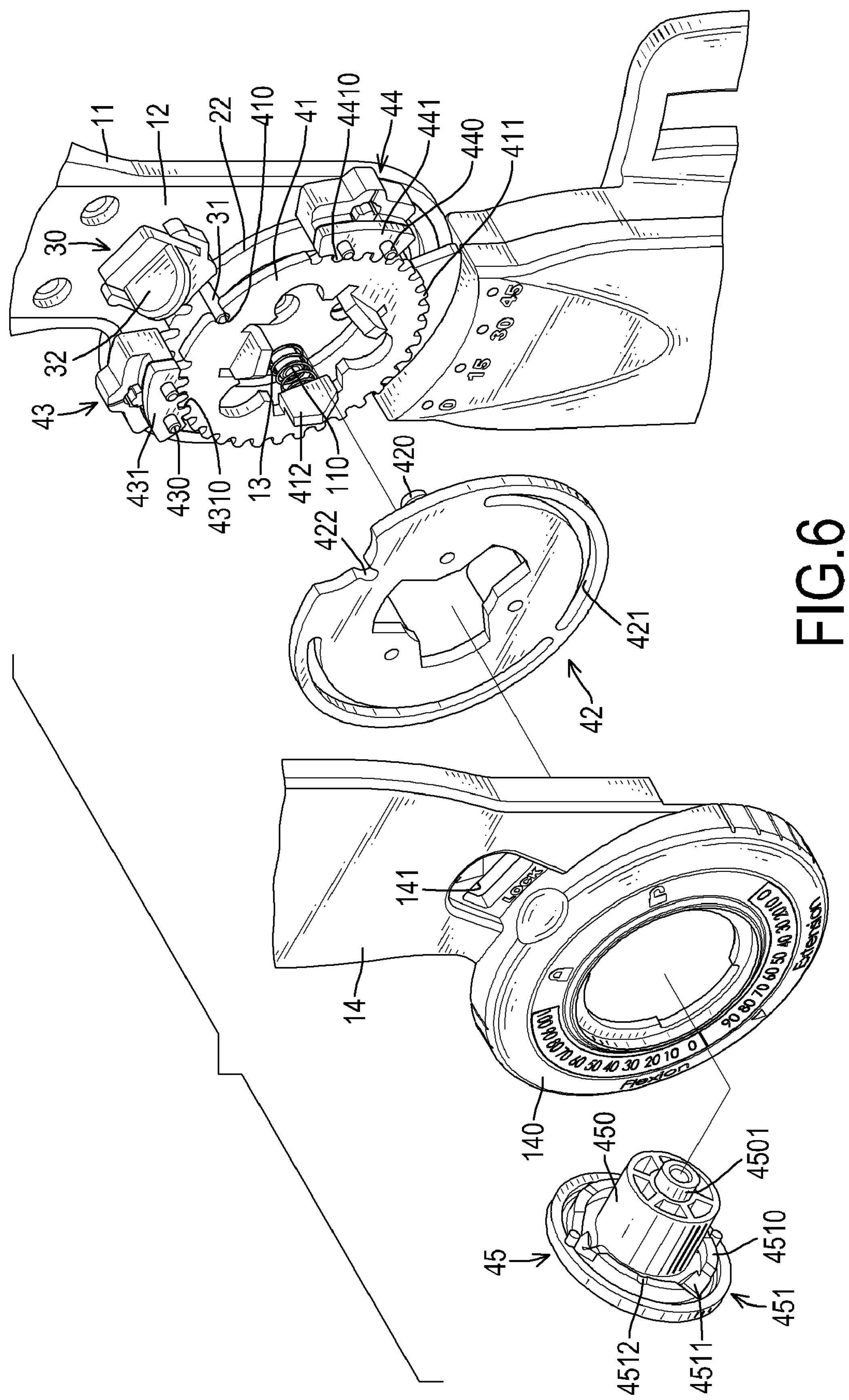
FIG. 6 is a partially exploded perspective view of the limiting connector for a knee brace in FIG. 1.
Figure 7:
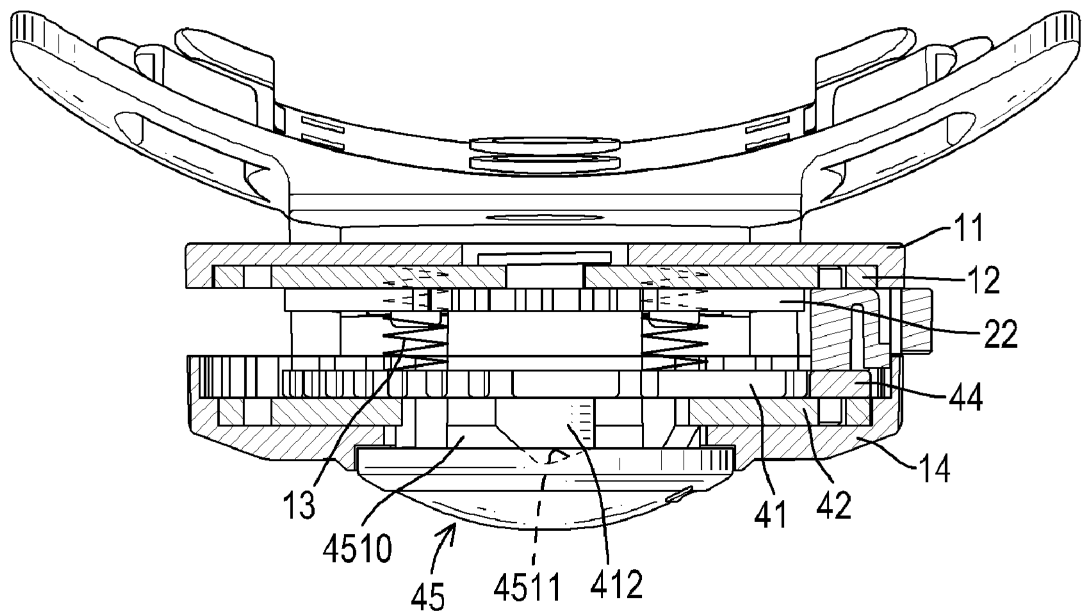
FIG. 7 is an enlarged operational top view in partial section of the limiting connector for a knee brace in FIG. 2.
Figure 8:
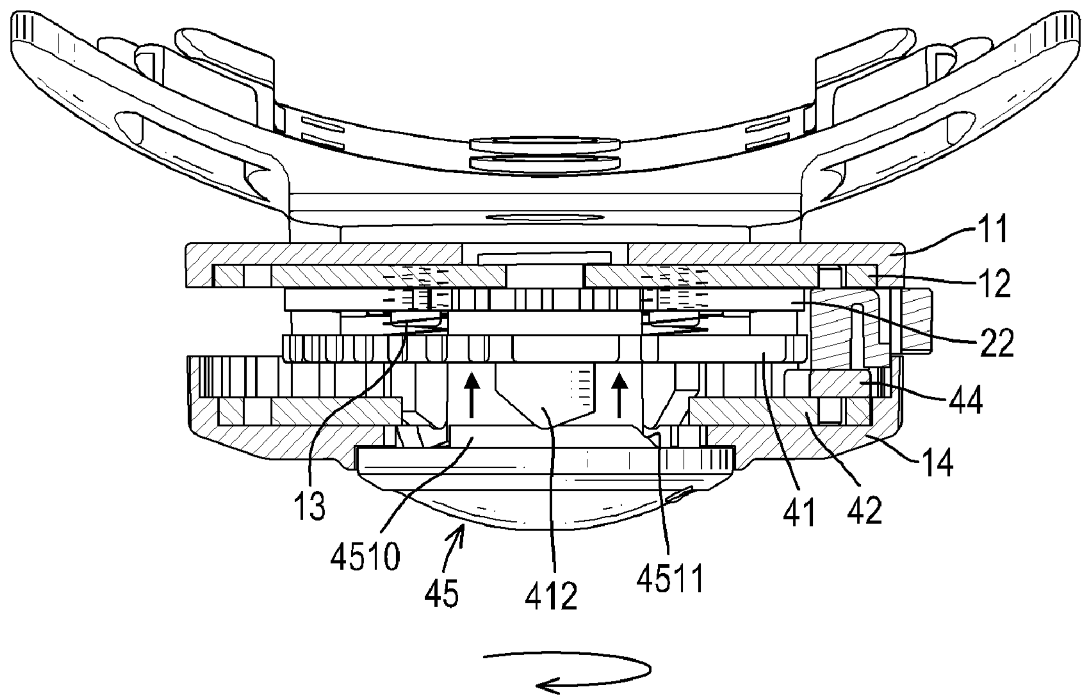
FIG. 8 is an enlarged operational top view in partial section of the limiting connector for a knee brace in FIG. 7.
Figure 9:
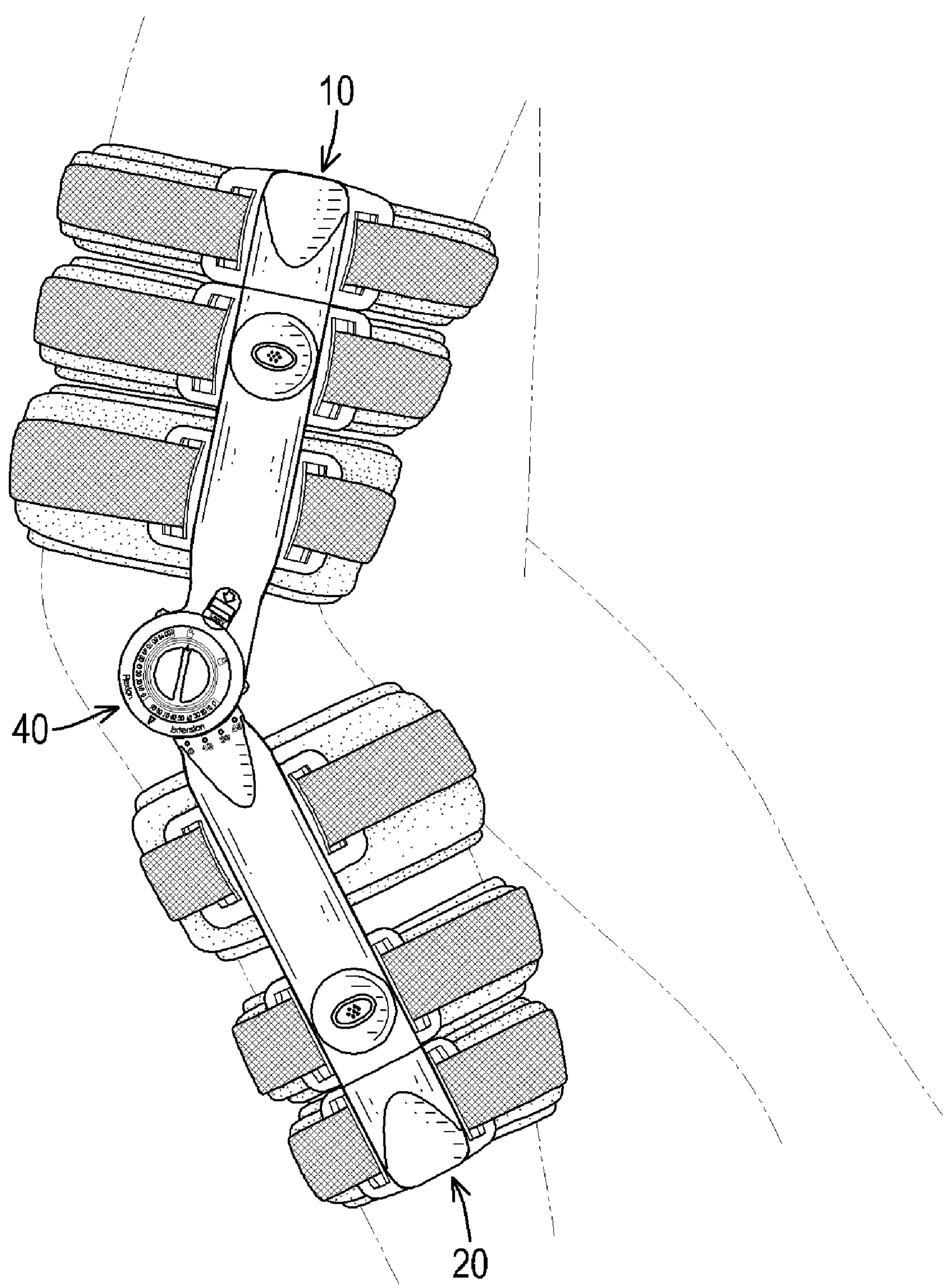
FIG. 9 is a perspective view of the limiting connector for a knee brace in FIG. 1 connected to a knee brace and mounted to a leg.
Figure 10:
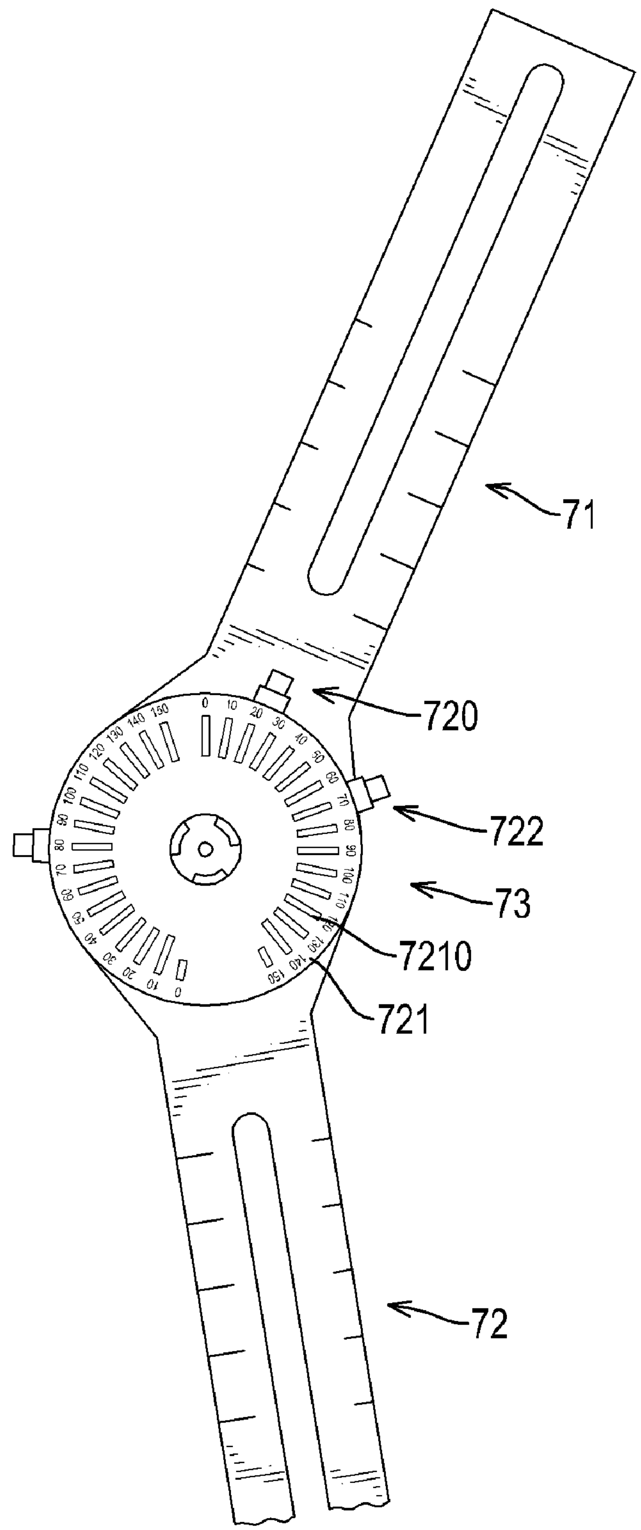
FIG. 10 is a side view of a conventional limiting connector for knee brace in accordance with the prior art.

With reference to FIGS. 5 and 6, in the first condition, the turning tab (32) of the lock (30) is pressed upward to make the locking pin (31) of the lock (30) disengages from the locking teeth (220) of the second pivoting element (22), the corresponding locking recess (410) of the positioning gear (41) and the corresponding locking mount (422) of the gear cap (42). The second arm (20) is pivoted and adjusted to a suitable angle relative to the first arm (10) according to needs of the user.

The turning tab (32) of the lock (30) is pressed down to mount the locking pin (31) of the lock (30) in one of the locking teeth (220) of the second pivoting element (22), a new corresponding locking recess (410) of the positioning gear (41) and a new corresponding locking mount (422) of the gear cap (42). Consequently, the first arm (10) and the second arm (20) can be kept at a fixed angle to provide a supporting effect to a leg of the user.

With reference to FIGS. 2, 3 and 6 to 9, the operation of the second condition has three steps. In the first step, the lock (30) is moved upward and held. The rotating cap (45) is rotated, and the pushing element (451) pushes the pressing element (412) of the positioning gear (41), and the second sliding surface (4511A) of each containing recess (4511) slides along the first sliding surface (4121) of the corresponding pressing protrusion (4120). When the rotating cap (45) is rotated to a position where the fixing recesses (4512) aligns with and engages the positioning surfaces (4123) of the positioning gear (41), the positioning gear (41) is pressed and moved toward the second pivoting element (22) and disengaged from the first button (43) and the second button (44).

In the second step, the first pin (430) of the first button (43) and the second pin (440) of the second button (44) are slid along the sliding rails of the sliding groove (123) of the first pivoting element (12) and the sliding channels of the sliding recess (412) of the gear cap (42) to define a swinging range between the buttons (43,44).

In the third step, the rotating cap (45) is rotated in reverse and makes the pressing protrusions (4120) of the positioning gear (41) mounted in the containing recesses (4511) of the rotating cap (45), and the first stopping surface of the pressing protrusions (4120) is abutted and stopped by the second stopping surface of the containing recesses (4511). The positioning gear (41) is pushed by the springs (13) and moved toward the gear cap (42). The positioning teeth (411) of the positioning gear (41) is engaged in the first button (43) and the second button (44). The second arm (20) is pivotally swung relative to the first arm (10) in the range defined between the first button (43) and the second button (44).

The limiting connector for knee brace has a lock (30) to hold the second arm (20) at a fixed angle relative to the first arm (10) and provides a fixed angular supporting function. Furthermore, the limiting connector for knee brace further has two slidable buttons (43,44) to define a swinging range to allow the second arm (20) to be pivoted and swung relative to the first arm (10) to provide a supporting effect during rehabilitation.

Even though numerous characteristics and advantages of the present invention have been set forth in the foregoing description, together with details of the structure and function of the invention, the disclosure is illustrative only Changes may be made in detail, especially in matters of shape, size and arrangement of parts within the principles of the invention to the full extent indicated by the broad general meaning of the terms in which the appended claims are expressed.

What is claimed is:

1. A limiting connector for knee brace comprising:

a first arm having
- a bar protruding from the first arm;
- a first pivoting element mounted around the bar of the first arm and having a sliding groove shaped as an arc and formed through the first pivoting element and along a sliding circle having a sliding center;
- a spring mounted on the bar; and a second arm connected pivotally to the first arm and having a second pivoting element shaped annularly and mounted parallelly on the first pivoting element and around the bar;

an angle adjusting assembly mounted between the first arm and the second arm and having
- a positioning gear shaped annularly, and mounted on the second pivoting element, and when mounted thereby abutting the spring, and further having
  - an outer edge;
  - an inner edge;
  - multiple positioning teeth formed in the outer edge of the positioning gear, and when the positioning gear is mounted, the multiple positioning teeth are adjacent to the sliding groove;
  - a pressing element formed on the inner edge of the positioning gear and having a pressing protrusion protruding perpendicularly from the inner edge of the positioning gear;
- a gear cap shaped annularly and mounted on the positioning gear around the pressing protrusion and having
- an inner edge;
- a fixing shaft protruding perpendicularly from the inner edge of the gear cap, and extending through the positioning gear and second pivoting element, and mounted on the first pivoting element;
- a sliding recess shaped as an arc and formed through the gear cap along a cap circle having a cap center aligning with the sliding center of the sliding circle; and a first button mounted between the first pivoting element and the gear cap and having
- a first pin mounted through the first button and having two ends respectively slidably extending into the sliding groove of the first pivoting element and the sliding recess of the gear cap;
- a first engaging teeth protruding from the first button and engaged to the positioning teeth of the positioning gear; and a second button mounted between the first pivoting element and the gear cap, and having
- a second pin mounted through the second button and having two ends respectively slidably extending into the sliding groove of the first pivoting element and the sliding recess of the gear cap;
- a second engaging teeth protruding from the second button and engaged to the positioning teeth of the positioning gear;

a rotating cap having
- an inner surface;
- a rotating shaft protruding from the inner surface of the rotating cap, and mounted through the gear cap, the positioning gear and the second pivoting element, and rotatably mounted on the first pivoting element;
- a pushing element protruding from the inner surface of the rotating cap around the rotating shaft, and having a containing recess formed in the pushing element and corresponding to and abutting the pressing protrusion of the positioning gear.

2. The limiting connector for knee brace as claimed in claim 1, wherein the sliding groove has two sliding rails;

the sliding recess has two sliding channels;

the two ends of the first pin of the first button are respectively extended into one of the sliding rails and one of the sliding channels; and the two ends of the second pin of the second button are respectively extended into the other sliding rail and the other sliding channel.

3. The limiting connector for knee brace as claimed in claim 2, wherein the first pivoting element further has a lock hole formed through the first pivoting element;

the second pivoting element further has a circular edge defined around the second pivoting element; and multiple locking teeth formed in the circular edge of the second pivoting element adjacent to the locking hole; and the limiting connector for knee brace further has a lock movably mounted in the locking hole of the first pivoting element and having a locking shaft selectively engaged in one of the locking teeth of the second pivoting element.

4. The limiting connector for knee brace as claimed in claim 3, wherein the pressing protrusion of the pressing element further has a top;

a first sliding surface formed slantwise on the top of the pressing protrusion; and the containing recess of the pushing element further has a second sliding surface formed slantwise in the containing recess, and corresponding to the first sliding surface of the pressing protrusion.

5. The limiting connector for knee brace as claimed in claim 4, wherein the pressing protrusion of the pressing element further has a first guiding surface formed slantwise on the top of the pressing protrusion, and having a length shorter than that of the first sliding surface;

a positioning surface formed between the first sliding surface and the first guiding surface;

a first stopping surface perpendicularly extending from the inner edge of the positioning gear and connected to the first guiding surface; and the pushing element further has a second guiding surface formed slantwise in the containing recess, and having a length shorter than that of the second sliding surface, and corresponding to the first guiding surface of the positioning gear;

a second stopping surface formed perpendicularly to the annular wall and connected to the second guiding surface, and abutting the first stopping surface of the pressing protrusions; and a fixing recess formed in the pushing element and selectively corresponding to the positioning surface of the pressing protrusion.

6. The limiting connector for knee brace as claimed in claim 5, wherein the first button further has a first slice mounted on the first button and having two first engaging teeth protruding from the first slice and engaging the positioning teeth of the positioning gear; and the second button further has a second slice mounted on the second button and having two second engaging teeth protruding from the second slice and engaging the positioning teeth of the positioning gear.

7. The limiting connector for knee brace as claimed in claim 1, wherein the first pivoting element further has a lock hole formed through the first pivoting element;

the second pivoting element further has a circular edge defined around the second pivoting element; and multiple locking teeth formed in the circular edge of the second pivoting element adjacent to the locking hole; and the limiting connector for knee brace further has a lock movably mounted in the locking hole of the first pivoting element and having a locking shaft selectively engaged in one of the locking teeth of the second pivoting element.

8. The limiting connector for knee brace as claimed in claim 1, wherein the pressing protrusion of the pressing element further has a top;

a first sliding surface formed slantwise on the top of the pressing protrusion; and the containing recess of the pushing element further has a second sliding surface formed slantwise in the containing recess, and corresponding to the first sliding surface of the pressing protrusion.

9. The limiting connector for knee brace as claimed in claim 8, wherein the pressing protrusion of the pressing element further has a first guiding surface formed slantwise on the top of the pressing protrusion, and having a length shorter than that of the first sliding surface;

a positioning surface formed between the first sliding surface and the first guiding surface;

a first stopping surface perpendicularly extending from the inner edge of the positioning gear and connected to the first guiding surface; and the pushing element further has a second guiding surface formed slantwise in the containing recess, and having a length shorter than that of the second sliding surface, and corresponding to the first guiding surface of the positioning gear;

a second stopping surface formed perpendicularly to the annular wall and connected to the second guiding surface, and abutting the first stopping surface of the pressing protrusions; and a fixing recess formed in the pushing element and selectively corresponding to the positioning surface of the pressing protrusion.

10. The limiting connector for knee brace as claimed in claim 1, wherein the first button further has a first slice mounted on the first button and having two first engaging teeth protruding from the first slice and engaging the positioning teeth of the positioning gear; and the second button further has a second slice mounted on the second button and having two second engaging teeth protruding from the second slice and engaging the positioning teeth of the positioning gear.

* * * * *